United States Patent [19]

Sneider

[11] 4,014,332
[45] Mar. 29, 1977

[54] DISPOSABLE SYRINGES
[76] Inventor: Vincent R. Sneider, 3422 Hillcrest Drive, Atlanta, Ga. 30319
[22] Filed: June 30, 1975
[21] Appl. No.: 592,037

Related U.S. Application Data
[63] Continuation-in-part of Ser. No. 389,506, Aug. 20, 1973, abandoned.
[52] U.S. Cl. .............................. 128/227; 128/232; 128/251
[51] Int. Cl.² ......................................... A61M 3/00
[58] Field of Search ... 128/251, 232, 227, DIG. 24, 128/239; 222/92, 106, 105

[56] References Cited
UNITED STATES PATENTS

| | | | |
|---|---|---|---|
| 1,123,361 | 1/1915 | Pease | 128/227 |
| 2,887,109 | 5/1959 | Barrington | 128/227 |
| 3,307,549 | 3/1967 | Zackheim | 128/227 |
| 3,476,111 | 11/1969 | Matheson | 128/227 |
| 3,724,461 | 4/1973 | Eisenberg | 128/227 |
| 3,818,910 | 6/1974 | Harris | 128/232 |
| 3,844,284 | 10/1974 | Schoenfeld et al. | 128/232 |

Primary Examiner—John D. Yasko
Attorney, Agent, or Firm—Ralph R. Roberts

[57] ABSTRACT

This invention contemplates a liquid filled sealable flexible bag having a manipulative discharge tube or nozzle. As a vaginal douche the discharge tube is removably equipped with a vaginal fitting which telescopically engages the tube. Positive closing means of the discharge tube is provided. The filled and plugged bag, complete with vaginal fitting, may be encased in a sealed envelope which in turn is conveniently accommodated in a purse-like flexible case. To use the device after breaking the sealed envelope, the vaginal fitting is removed and the douche is ready for administration. In addition to the syringe there is disclosed an enema bag and including manipulative valve shutoff means.

7 Claims, 21 Drawing Figures

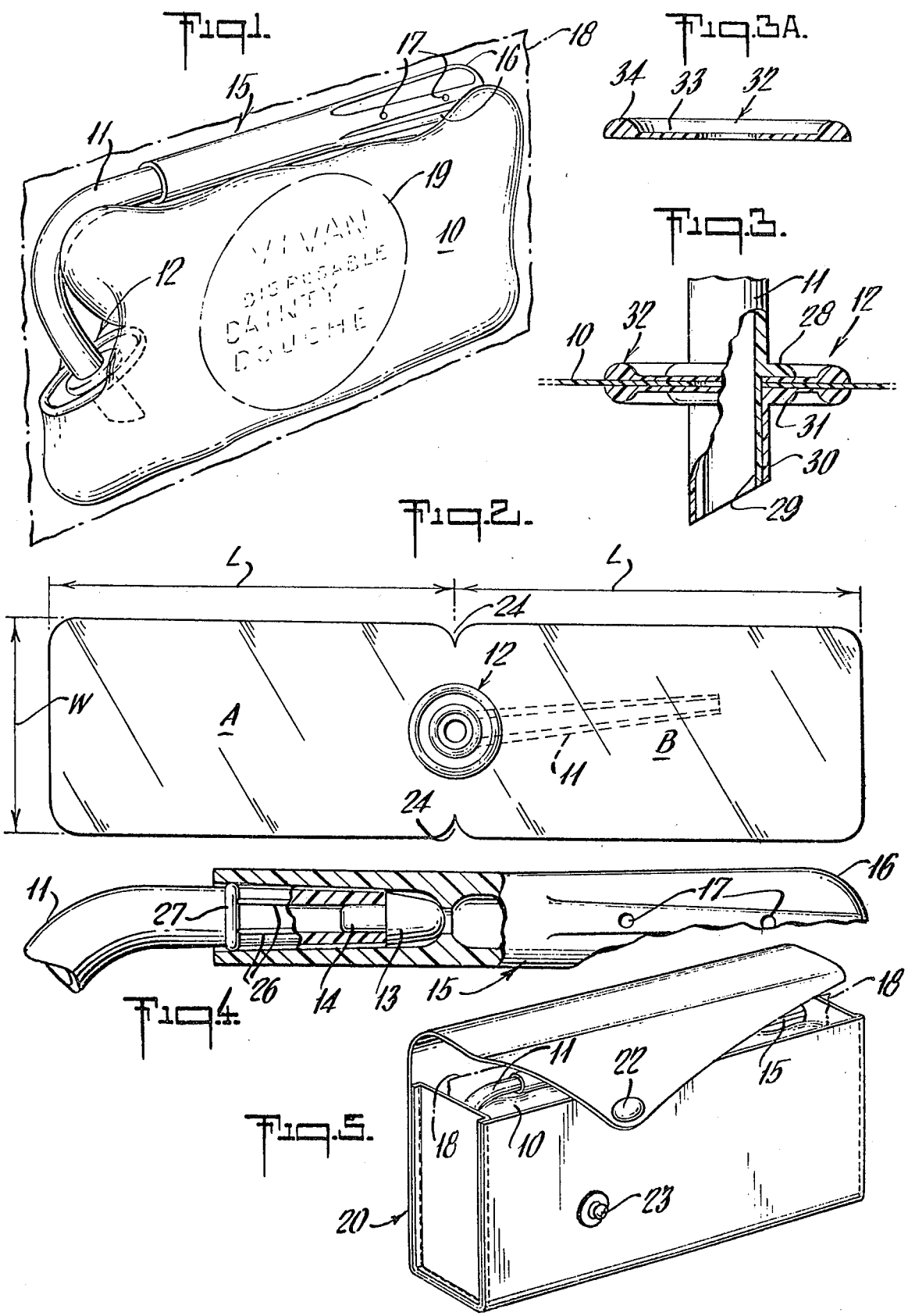

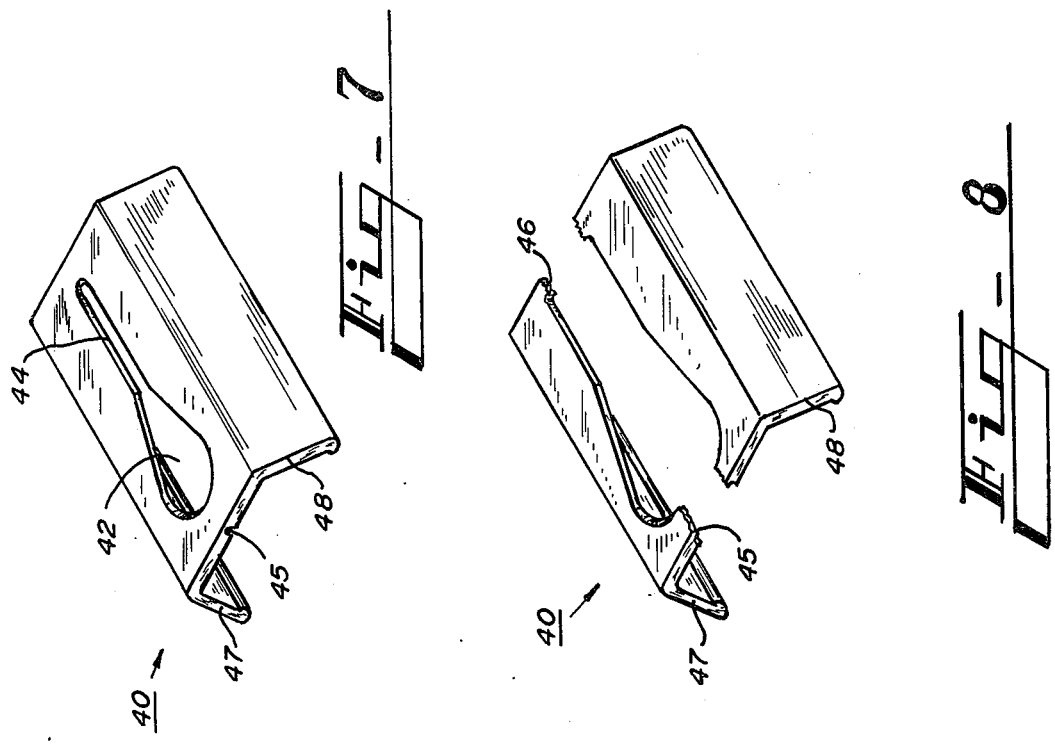
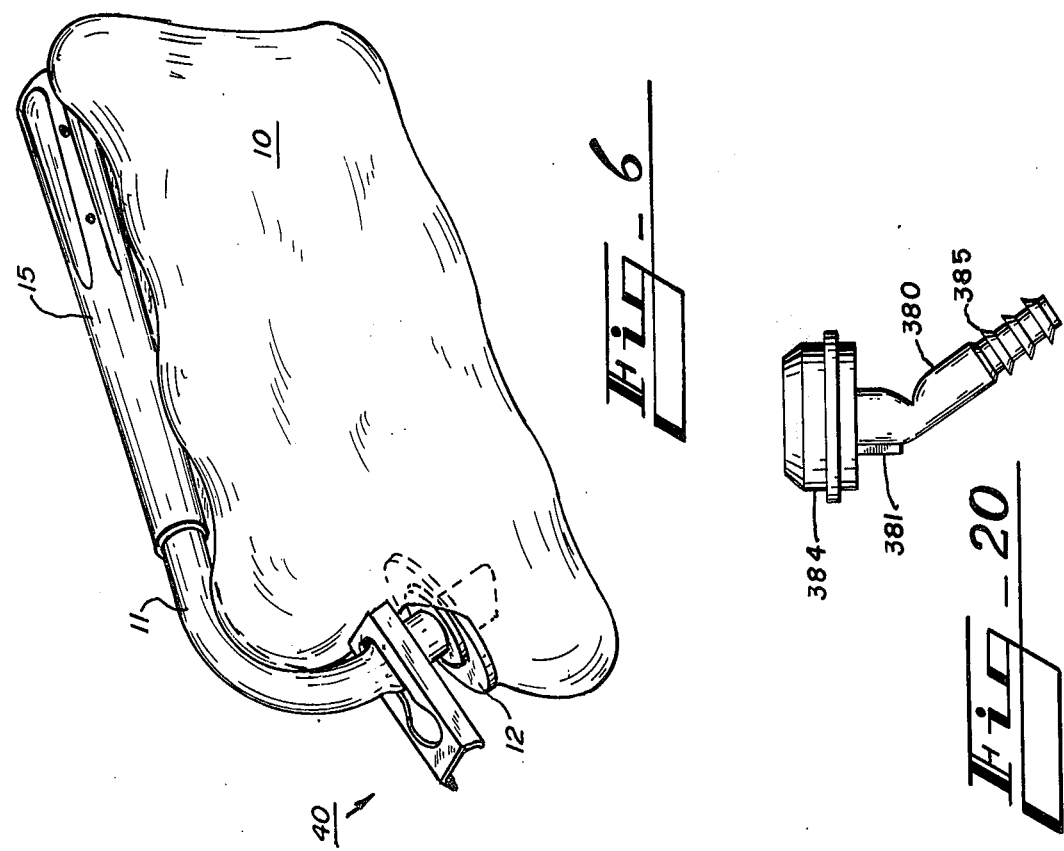

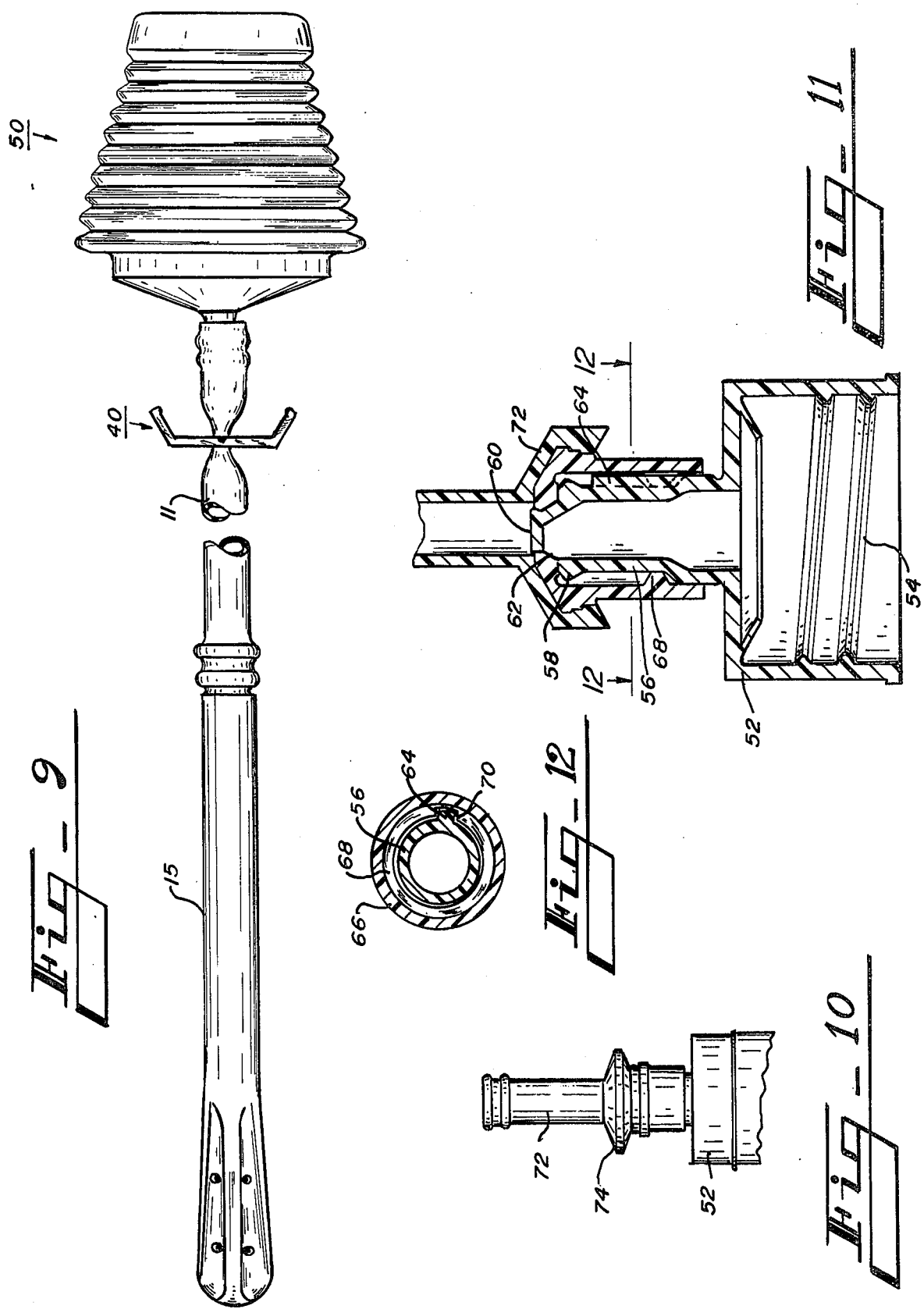

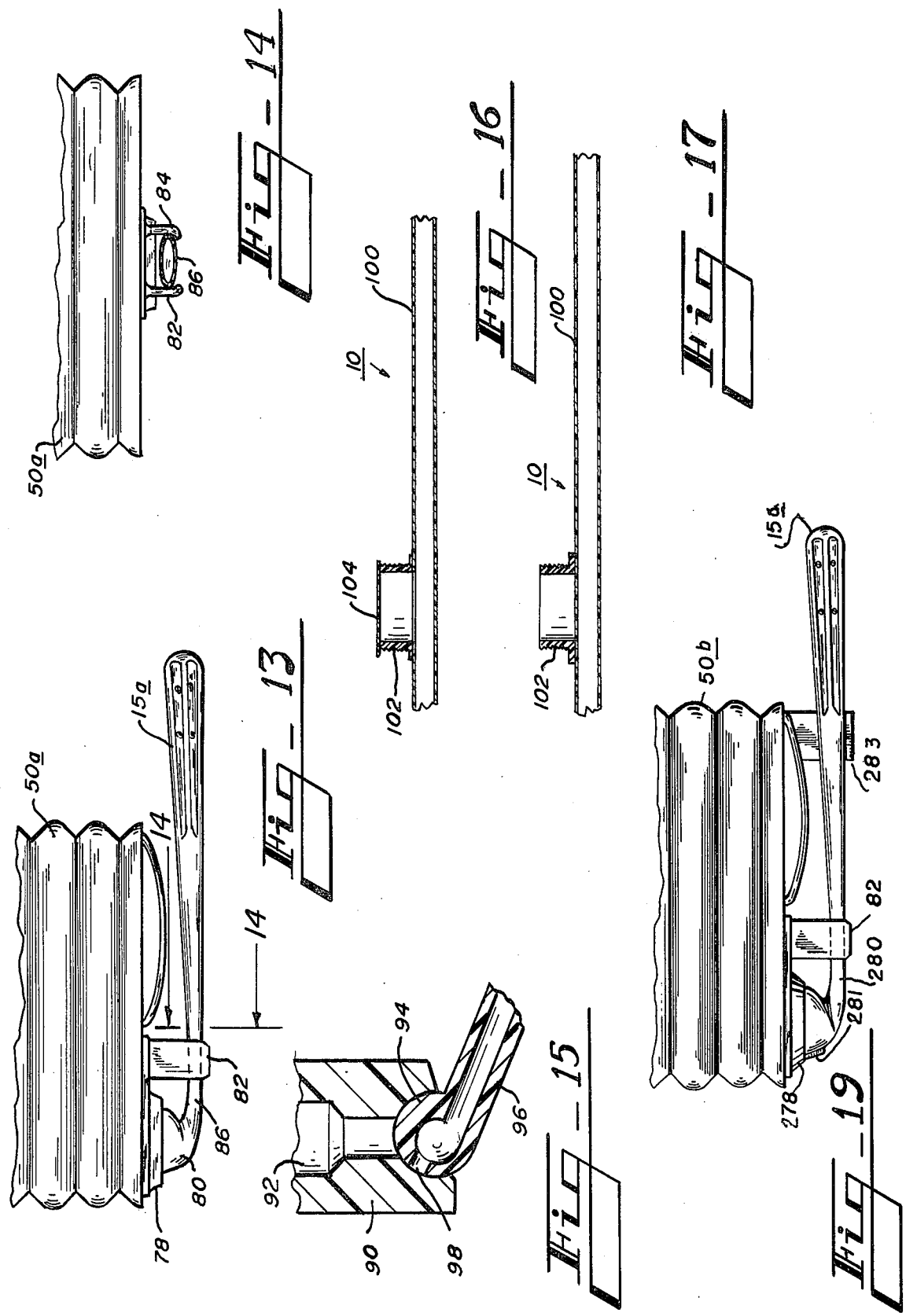

DISPOSABLE SYRINGES

CROSS REFERENCE TO RELATED APLICATIONS

This application is a Continuation-in-part of my U.S. patent aplication, Ser. No. 389,506, filed Aug. 20, 1973 and now abandoned.

BACKGROUND OF THE INVENTION

1. Field of the Invention

This invention pertains to the field of art found generally in the Class of Surgery and more particularly in the subclass of "douches" and even more particularly in the subclass of "vaginal douches".

2. Description of the Prior Art

Prior douche devices have operated on the theory of reusability or on the theory of ready assembly of a kit of parts importantly including a flexible bag which must be filled with liquid prior to completion of assembly, all before the device is ready for use. Even so-called disposable douches contemplate local mixing of medicaments in water, before completing the assembly.

Among the patents pertaining to syringes are U.S. Pat. No. 2,784,716 to BROMAN on Mar. 12, 1957; U.S. Pat. No. 2,811,968 to HYATT as issued on Nov. 5, 1957; U.S. Pat. No. 3,177,871 to MEYERS as issued on Apr. 13, 1965 and U.S. Pat. No. 3,626,939 as issued to MALTENFORT on Dec. 14, 1971. In view of these and other known patents the compact disposable syringe with wrapper and flow control means as shown and described in the following application is believed to be novel.

SUMMARY OF THE INVENTION

This invention may be summarized at least in part with reference to its objects.

It is an object of the invention to provide an improved douche, enema or the like syringe construction which does not require liquid mixing or filling just prior to use.

Another object is to provide such a construction and method of construction that will represent extreme low cost, consistent with the ruggedness needed to safely contain a premixed, suitably medicated liquid filling, regardless of the mechanical shock which is unavoidable in shipping, retailing and other necessary handling, between manufacture and customer use.

A further object is to achieve the above objects with a structure wherein there may be utmost convenience and ease of use, as well as virtually total discharge of the liquid contents.

A still further object is to provide an improved douche, syringe.

A further object of the invention provides for tubing shutoff means which in one embodiment incorporates a keyhole-type of tubing closure, said closure member having means for the ready breaking thereof. In another embodiment the tubing closure includes bending the tubing and holding the tube in a flattened, sealed condition. An alternate shutoff valve is a rotary swing-type valve. Another valve includes longitudinal movement to open the valve and combined therewith is a rotary lock to prevent accidental and unwanted closure of the valve.

Other objects and various further features of novelty and invention will be pointed out or will occur to those skilled in the art from a reading of the following specification in conjunction with the accompanying drawings.

In said drawings, which show, for illustrative purposes only, a preferred form of the invention:

BRIEF DESCRIPTION OF THE DRAWINGS

FIG. 1 represents a perspective view of a filled syringe of the invention, as packed at the factory, in a sealed, pliable plastic envelope suggested by phantom outline;

FIG. 2 represents a plan view of the syringe bag of FIG. 1, prior to the seaming by which its assembly is completed;

FIG. 3 represents an enlarged fragmentary view at juncture of a discharge-tube part to the syringe bag, the same being partly broken away to reveal a longitudinal section along the axis of juncture;

FIG. 3A represents a sectional view of a washer part;

FIG. 4 represents a fragmentary view, also partly broken away and in section, to show nozzle structure for vaginal douche application;

FIG. 5 represents a perspective view of a carrying case for the product of FIG. 1;

FIG. 6 represents a perspective view of a syringe similar to that of FIG. 1 but including a keyhole-type of tubing clamp secured to and shutting off the flow of fluid from the envelope and through the tubing;

FIG. 7 represents an enlarged perspective view of the keyhole clamp of FIG. 6;

FIG. 8 represents a perspective view of the clamp of FIG. 7 after it has been broken by bending at preweakened score lines;

FIG. 9 represents a side view of a bellows-type of syringe in which the breakable keyhole-type of tubing clamp of FIG. 7 is mounted on the tubing adjacent the outlet of the syringe;

FIG. 10 represents a side view of an alternate valve means in which longitudinal motion is employed to open the valve;

FIG. 11 represents in a greatly enlarged scale a sectional view of the valve means of FIG. 10;

FIG. 12 represents a sectional view taken on the line 12—12 of FIG. 11 and looking in the direction of the arrows;

FIG. 13 represents a fragmentary side view of the bellows syringe of FIG. 9 but with an alternate fluid shutoff means in which the tubing is shaped so that when bent to approximately a right angle the tubing is caused to be flattened to shut off flow through the tubing;

FIG. 14 represents a view taken on the line 14—14 of FIG. 13 and looking in the direction of the arrows, this view showing a means for retaining the tubing in a bent and flow shut off condition for shipment and storage;

FIG. 15 represents a fragmentary sectional side view of yet another type of shutoff valve;

FIG. 16 represents a fragmentary, partly diagrammatic side view of an inlet closing means for an envelope which is to be filled with water at time of use;

FIG. 17 represents a fragmentary, partly diagrammatic side view similar to that of FIG. 16 but with an alternate envelope closing means;

FIG. 19 represents a fragmentary side view of the bellows syringe of FIG. 13 but with the fluid conduit being of round configuration and having a pair of stiffening ribs extending outwardly from one side and causing the tubing to pinch closed when bent at approximately a right angle, and FIG. 20 represents a side view of the fluid shutoff of FIG. 19 but with the valve means adapted to receive and retain a length of tubing of conventional flexible construction.

In the following description and in the claims various details are identified by specific names for convenience. These names, however, are intended to be generic in their application. Corresponding reference characters refer to like members through the several figures of the drawings.

Figure 18:
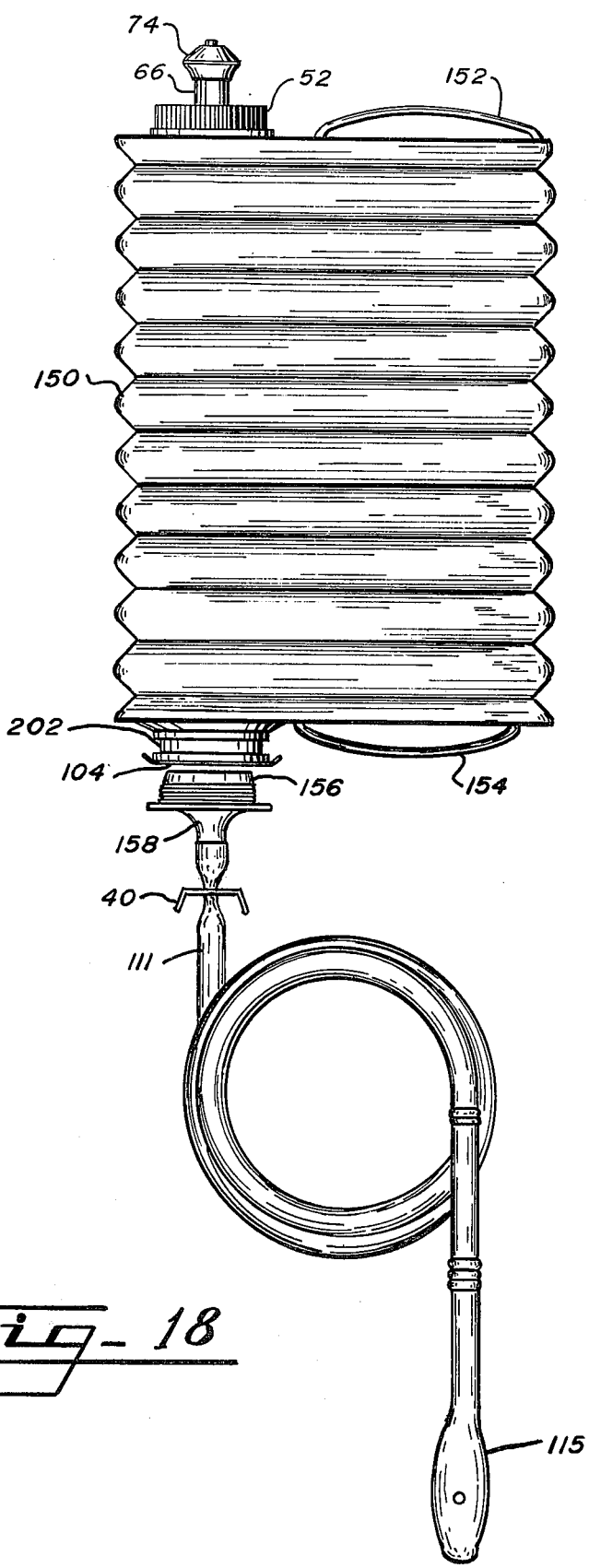
FIG. 18 represents a partly diagrammatic side view of an accordion-type enema syringe having a sealed outlet and a valved inlet by which the air flow is regulated or shut off.

The drawings accompanying, and forming part of, this specification disclose certain details of construction for the purpose of explanation but it should be understood that these details may be modified in various respects without departure from the concept and that the invention may be incorporated in other structural forms than shown.

DESCRIPTION OF THE EMBODIMENT OF FIGS. 1 THRU 5

In FIG. 1 the article shown comprises a liquid filled, sealed envelope or bag 10 of tough pliable heat sealable plastic material such as polyethylene of about 5-mil. thickness. Bag 10 is elongated and of generally rectangular plan form having a length which may approximate twice its width. At one longitudinal end a liquid dispensing conduit, tube or fitting 11 is secured at a flexible reinforced region 12 and provides liquid communication for discharge of the contents of the bag 10. A plug 13 having a reduced stem 14 (FIG. 4) in frictional engagement with the discharge end of conduit 11 preserves the sealed relation of the bag 10 which in this embodiment is prefilled with liquid appropriate to the intended use, as for example suitably medicated and scented for vaginal douche purposes or otherwise compounded for use as an enema. Generally a 5 ounce volumetric capacity is satisfactory so that a filled bag 10 is about an inch thick, 2 inches wide and 4 inches long.

For vaginal douching it is preferred to supply a nozzle fitting 15 which is shown as a simple injection molded plastic part as of high density polyethylene. This nozzle has elongated ridge formations or flutings 16 between discharge openings 17 at the discharge end. The remainder of fitting 15 is tubular to define a bore for telescoping placement over plug 13 and into lightly frictional engagement with the outer inch or so of the conduit 11. As shown, plug 13 has an outer diameter slightly less than that of the telescope fitted end of the bore of fitting 15 and a slight local reduction in this bore diameter at 18 enables a stop engagement with the enlarged end of plug 13 to limit the telescopic assembly.

In the form shown, assembly is completed by enclosing the filled bag 10 complete with assembled nozzle fitting 15 (if intended as a douche) in an outer protective sealed envelope 18 of flexible, preferably transparent plastic material such as 0.5 mil. polyethylene whereby sterility of contents is assured and further whereby the tube 11 and its nozzle 15 will be retained in nested adjacency to and along a longitudinal edge of bag 10. As shown, the preferred overall effective length of tube 11 is less than that of the filled bag 10 and in fact when assembled to nozzle 15 the effective overall length of parts 11–15 is at least no greater than that of the filled bag.

As thus described, the filled, sealed and sterile assembly is suitable for certain channels of sale as, for example, automatic sale at vending machines, the transparent envelope 18 providing clearly readable access to product marking, instructions or the like already printed on the bag 10 as suggested at the region 19. Alternatively as shown in FIG. 5, the product of FIG. 1 lends itself to discreet protected packaging in a simple elongate carrying case 20 of generally rectangular prismatic shape and having a single closure flap 21 to provide access to the article along an upper longitudinally extending edge. Flap 21 is shown detachably securable by snap engagement of means 22–23 on one of the large side panels which does not include the flap 21. Case 20 will be understood to be appropriately dimensioned for purse portability.

In use the sealed envelope 18 need only be broken and discarded and nozzle 15 briefly removed to provide fingernail access for dislodgement of plug 13; whereupon nozzle 15 is replaced and the douche is ready for application. Since the bag 10 is so pliable all the way to the locus 12 of conduit attachment it is possible to fully compress the bag and thus expel virtually the entire liquid contents. All parts are then discarded as refuse.

FIGS. 2 and 3 provide illustration of methods of making the described bag 10. According to one technique the plastic sheet material of the bag 10 is precut to a blank of the necessary extent as to the elongate generally rectangular outline shown in FIG. 2 wherein the overall length is twice the intended length L of the bag prior to filling and wherein the width dimension W is the width dimension of the bag prior to filling. Preferably outer corners are gently rounded, as shown, and cusp-like cut-outs 24 are made at center locations of both longitudinal edges of the blank with cusp curvatures matching the outer corner curvatures. A center fold axis is thus defined between cusps 24 thus also identifying the two panels A–B which ultimately become the opposite side panels of the completed bag.

Before folding, however, the discharge conduit 11 is assembled and secured to the blank centrally of the intended fold alignment, that is, preferably at intersection of diagonals of the blank. FIG. 3 serves to illustrate one method of accomplishing such assembly wherein conduit 11 is an injection molded stiffly flexible tube which slightly tapers from location 12 to a reduced discharge end to accommodate plug 13. As shown in FIG. 4, elongate longitudinal ribs 26 lead to a peripheral bead 27 on the outside of tube 11 near its discharge end thereby assuring frictional engagement and retention of nozzle 15 as well as a leak-tight seal at bead 27. The mounting region of conduit 11 includes a small radial flange 28 and a reduced end 29 of length sufficient to accommodate assembly of a retaining sleeve 30 having an integral flange 31 corresponding to and axially opposed to flange 28. Using such parts as well as two washers 32, shown in FIG. 3A, to comprise an annular panel 33 of flexible sheet (e.g. polyethylene) and a peripheral bead 34 of semicircular section the assembly is made to the flattened blank of FIG. 2; in such assembly the first or upper washer 32 is seated against the shoulder defined by flange 28 while reduced end 29 extends through a small local opening in the blank. The other washer 32 is applied in opposed relation to the upper washer 32 and against the lower surface of the blank and is located on the reduced end 29. Finally, the sleeve fitting 30 is applied. The described assembly of parts may be completed using adhesive to secure all adjacent surfaces (interfaces) resulting in a reinforced, universally flexible, liquid-tight mounting of the tube 11 to the blank. Preferably, however, suitable dies, including heated extremities, are applied to axially load or squeeze the washers 32 into permanently heat sealed unison with the region of the bag blank compressed therebetween; at the same time the telescoped engagement at 29–30 may be heat bonded or sonic welded.

Bag assembly is then completed by folding panels A–B against each other and in registry, while applying matched heat sealing dies to compress and heat seal the panels to each other at the outer edge of the bag, the extent of such peripheral welding, of course, being only as necessary to complete the liquid tight integrity of the bag. Thus the bonded region may commence at opposite sides (i.e., the A-panel side and the B-panel side) of the upper cusp 24 of FIG. 2, proceeding thence along the upper registered longitudinal edges of these panels around their matched rounded upper outer corners, down their matched outer transverse edges, around their matched rounded lower outer corners, along their lower matched longitudinal edges and around the matched opposite sides (i.e. the A-panel side and the B-panel side) of the lower cusp 24. Thus constructed bag 10 is complete and liquid-tight, relying upon the fold between cusps 24 to complete the peripheral integrity of the closure and no offal need be trimmed.

While the bag 10 is still flat it is liquid filled with medicating, perfuming and like antiseptic components via the tube 11. The flat initial condition assures against air displacement as a filling problem. And the filled article is plugged, fitted and packaged as already described.

In an alternative method of bag assembly the flank outline is not critical as long as the desired ultimate folded bag profile is realizable. In such alternative the tube 11 is assembled to the sheet material of the bag at a location to permit folding to achieve the desired bag area. The blank (with attached tube 11) is then folded, preferably to include region 12 near the fold and the heated peripheral seal dies are applied to establish bag closure to desired contour. Thereafter or concurrently with heat sealing of the periphery, the completed article is severed by appropriate cutting dies which may be part of the heat seal die structure, as will be understood.

This improved douche, enema or the like syringe device, construction and method is achieved with extreme economy of materials and manufacturing cost. At the same time utmost ease and convenience of use are afforded.

TUBING SHUTOFF OF FIGS. 6, 7 AND 8

Referring next to FIGS. 6, 7 and 8, it is to be noted that a bag like that of FIG. 1 is shown. The reinforced region 12 and the connecting tube 11 to nozzle 15 is also shown. Rather than the removable plug 13 of FIG. 4 above-described, there is provided in this embodiment a keyhole-type clamp generally indicated as 40. This clamp is preferably made of plastic which may be extruded, molded or may be die cut and formed and includes a tear-shaped opening 42 which merges with a narrow slot 44. The combined aperture extends substantially the longitudinal length of the nozzle clamp. Small bridge portions are left at either end of this aperture and maintain a transverse support of the clamp 40. The sides of this clamp are turned downwardly at approximately 60° to provide manipulating means which may be squeezed to cause a bending pressure to be brought upon weakened area 45 and 46. These areas in the present instance are small or shallow grooves formed in the mid or planar surface portion of the clamp 40. It is contemplated in the manufacture of this item that the clamp may be an extruded piece of plastic with grooves 45 and 46 formed as part of the extrusion process. As a secondary operation a cutoff and punching of the aperture opening provides the tear-shaped opening 42 and the slot 44.

USE AND OPERATION

Assuming that the bag 10 is filled prior to the attachment of the nozzle 15 the keyhole clamp 40 is slid onto the tubing 11 with the tear-shaped opening 42 providing means for moving the clamp to its desired position before closing the tube by moving the tube into slot 44. After the filling has occurred the slot portion 44 is caused to be moved over the tubing portion 11 to flatten the tubing into a sealed condition whereat the fluid contents of the bag is maintained for shipment and/or storage and until such time as the contents of the syringe are to be expelled. At the time of use, the nozzle 15 is positioned as desired whereupon the user merely grasps the sloped sides 47 and 48 and urges them toward each other. At the weakened portions 45 and 46 the clamp breaks and forms two portions as seen in FIG. 8. The contents of the bag may then be forced through the tube 11 as required and desired.

ALTERNATE EMBODIMENT OF THE SYRINGE OF FIG. 9

Referring next to the embodiment seen in FIG. 9, it is to be noted that instead of the flat bag 10, as seen in FIGS. 1 and 6, there is provided a small accordion-type container identified generally as 50. This accordion container 50 has a discharge end to which is secured the tubing 11. On this tubing is mounted the nozzle 15 as seen in FIG. 1. The keyhole clamp 40 is placed upon the tubing 11 as in the unit of FIG. 6. The keyhole-type clamp 40 is then manipulated or squeezed so as to be broken apart to release the contents of the container 50 when it is to be used.

SLIDING VALVE OF FIGS. 10, 11 and 12

Referring next to FIGS. 10, 11 and 12 there is shown an alternate valve means which provides a fluid cutoff but instead of the keyhole clamp 40 this fluid cutoff valve is opened by a pulling or longitudinal motion. As seen in FIG. 10, a cap portion 52 may have internal threads 54 as in FIG. 11. The upper portion of this cap 52 is connected to a tubular conduit 56 which has a reduced portion intermediate its inner end and an outwardly enlarged stop ring which is provided at the upper or terminal end. This upper stop ring is generally identified as 58. A tapered closure portion identified as 60 has an aperture portion 62 therein and therewith provides an outlet passageway from the interior of the tubular conduit portion 56. A longitudinal key member 64 is shown as formed on the side of said tubular portion 56. This key member terminates short of the outer upper retaining ring portion 58. A sliding outer sleeve member 66 has an internal collar portion 68 which collar portion is slidable upon the outer diameter of the midlength of the inner tubular conduit 56. This collar 68 as and when it engages the upper retaining ring 58 formed on the conduit 56 is in interference with this ring thus preventing further outward travel. A keyway 70 is formed in this internal collar portion 68 and is compatible with and is slidable along the longitudinal key 64 until it arrives at the end of the key whereupon the internal collar portion 68 becomes disengaged from the key. The undersurface of the internal collar portion 68 when the sleeve member is rotated slightly then engages the end of the longitudinal key 64 and is thereby prevented from rearward movement of the outer sleeve member 66. Connector 72 is mounted on the upper portion of the sleeve member 66 and may be a portion of the plastic tubing or may be adapted to receive tubing. As seen in FIG. 10, if desired, an enlarged finger gripping ring 74 may be provided as a portion or a part of connector 72. This finger gripping ring provides manipulating means for moving the outer sleeve member 66 in and out. The inner top portion of sleeve 66 is contoured to provide a sealing engagement with the end of the inner tubular conduit 56 to prevent fluid flow through aperture 62 when the sleeve member 66 is in the inner position, as seen in FIG. 11.

USE AND OPERATION OF THE VALVE OF FIGS. 10, 11 AND 12

As depicted, a sliding valve as seen in FIGS. 10, 11 and 12 may be used with the accordion container as seen in FIG. 9 and in accordance therewith a screw or a similar attachment means is provided on the end of the accordion container by which and after the container has been filled the valve member of FIGS. 10, 11 and 12 may be secured thereto. When the outer sleeve member 66 is pushed to its inner sealing condition, as seen in FIG. 11, the upper end portion of this sleeve member seats upon the tapered upper closure portion of the inner tubular conduit connector 56. In this inner condition the keyway 70 has been mated with the longitudinal key 64 so that member 66 can only be pulled outward and there is an absence of rotational movement. When this sliding valve is to be opened the manipulating ring 74 is grasped or the connector 72 is grasped and pulled outwardly until the internal collar portion 68 has passed beyond the end of the key 64 after which a slight rotation of the sleeve member 66 causes the lower surface of the internal collar 68 to engage the end of the key 64 which acts as a stop to prevent inward movement and unwanted shutoff of the valve. This is particularly advantageous when a short douche-type syringe is provided such as the syringe which is preferably nearly full size, as shown in FIG. 9, and when the sliding valve of FIG. 10 replaces the keyhole clamp 40 of FIG. 9.

ALTERNATE VALVE ARRANGEMENT OF FIGS. 13 AND 14

Referring next to FIGS. 13 and 14 there is shown a valve shutoff used with a bag which may be an accordion-type container identified as 50a. There is attached to the lower portion an adapter 78 which carries the lower end of a flexible conduit 80. This conduit is formed with an elliptical cross section. This elliptical cross section, when bent to the condition of FIG. 13, causes the two sides to flatten and closes the tube to prevent the flow of fluid therethrough. This elliptical tubing may be retained in its closed condition by means of gripping fingers 82 and 84, the elliptical tubing portion 86 may be molded as part of a nozzle 15a or may be otherwise secured to a nozzle. When the elliptical tubular portion 86 is folded or bent to the condition, as seen in FIG. 13, at the maximum point of the bend the two longer sides come together to form a fluid shutoff. When the nozzle 15a and the tubular portion 86 are swung outward from the gripping condition provided by the opposed fingers 82 and 84, the fluid may be pushed or otherwise expelled from the bag or container 50a.

Whether the fluid is to be carried in the container or is to be added later, the simple cutoff provided by folding the elliptical tubular portion into a flattened condition causes it to shut off the fluid and is an inexpensive means for providing a cutoff valve. Whether the nozzle 15a is attached immediately thereto or to an additional length of conduit extending for a distance immediately past the gripping fingers 82 and 84 is merely a matter of selection.

ALTERNATE VALVE MEANS OF FIG. 15

In FIG. 15 there is depicted a rotary or swing valve in which is an adapter body 90 which may be permanently fastened or otherwise secured to the bottom of a container such as the container 50, seen in FIG. 13. In this alternate valve means is provided a fluid conduit member 92 which terminates at a arcuate recess 94. This arcuate recess preferably has flat or parallel side walls into which a complementary-formed portion having a conduit 96 is rotatably retained. An aperture 98 at the upper end of this conduit 96 is closed when said conduit is turned more than ⅛ turn and is opened to the flow path 92 when the conduit is swung in more-or-less alignment so that the aperture 98 is brought in way of the flow path 92. A swing valve of like construction is commonly found with lighter fluid and oil can containers and the like. The adapter body 90 may be positioned so that gripping fingers 82 and 84 may engage and retain the conduit portion 96 to retain the conduit in a shutoff condition during shipping and storage. At and during time of use the conduit 96 is moved from its retained condition.

CONTAINER SEALING MEANS AS SEEN IN FIG. 16

It may be desirable that the bag 10 of FIGS. 1 and 6 be shipped absent the liquid and with only a powder component enclosed therein. It is thus desirable that a seal of the powder be provided. One means is shown whereby a seal is provided which may be easily broken by piercing means. On a side wall 100 of the bag there is secured as by heat sealing a collar member 102. The outer rim surface portion of said collar has a thin plastic member 104 placed over it after the powder has been placed in the bag. This member 104 is thus sealed to the rim. This plastic member is easily pierced and by a sharp cutting portion provided by a cap member, not shown. This cap member, after the fluid has been placed in the bag, closes the bag by being tightened upon the threaded portion of the adapter 102. In this embodiment the aperture in side wall 100 is shown as being pierced prior to or subsequent to the securing of the adapter 102 to side wall 100.

BAG CONSTRUCTION AS SEEN IN FIG. 17

As seen in FIG. 17, the side wall 100 of the bag 10 instead of having an aperture formed therein, as in FIG. 16, the wall is left in an uncut condition and then is sealed to the adapter collar 102. In this particular embodiment no exterior seal 104 is provided and the film portion of the side wall 100 extends across the opening of the adapter 102 providing the initial seal of the bag. It is assumed that the powder is placed in the bag before one or several edges of the bag are finally sealed. At the time of adding the fluid the portion of the side wall 100 within the adapter 102 is pierced by a cutting means so that fluid may be added to the bag. After the fluid is added, a threaded cap, not shown, is mounted on the adapter 102 to retain the contents in the bag.

CONTAINER ASSEMBLY AS SEEN IN FIG. 18

Referring next to FIG. 18 there is depicted an accordion-type container 150 which as shown has the ends preferably molded with finger gripping handle portions 152 and 154. These handles provide means by which the accordion bag may be manipulated for both expanding and collapsing the container. To the lower wall of the container 150 there is shown an attached adapter portion 102 on which is secured a sealing member 104. As contemplated, this sealing member is a thin plastic member 104 and is pierced by the sharp edge of a conical portion 156 of the tubing adapter 158. This adapter is a push-in fit in adapter 102. On a length of tubing 111 is shown a keyhole-type clamp 40 or, if desired, a longitudinal sliding clamp as shown in FIG. 10 may be used. The upper end of this accordion container 150 is shown with a threaded cap 52 which carries a longitudinal valve such as that of FIG. 10. This valve has the finger gripping ring portion 74 by which the sleeve member 66 is moved outward. This valve may or may not have a longitudinal key 64 since it is the intention of this valve to provide a separately controllable air inlet to the interior of the container. This valve is opened and closed to the passage of air to the interior of the container 150.

USE AND OPERATION OF THE ENEMA ARRANGEMENT OF FIG. 18

It is contemplated that this enema assembly may initially contain a powder such as the barium powder used for certain types of enemas. This powder is sealed by the plastic barrier 104 and by the closure of the upper air valve. This assembly conventionally is shipped in two parts requiring a minimum of space. The keyhole clamp 40 preferably is in place to close the tubing portion 111. Also assembled and shipped as a part of the tubing assembly is a nozzle portion 115 which is contoured for the intended use. When a rectal use is contemplated the nozzle will have a slightly different configuration than when for vaginal use. At the time of use, the sharpened edge of the tapered portion 156 will be used to pierce the plastic seal 104. By means of frictional engagement the adapter portion 158 is mounted in the interior portion of the adapter 102. The screw cap 52 is turned and removed from the accordion container 150 whereupon the desired amount of liquid is now poured into the container. The cap 52 is then reapplied and tightened. The contents are then shaken for mixing prior to administration to the patient. After the proper placement of the nozzle 115 the clamp 40 is broken to allow fluid to pass through the tubing 111 and to the end of the nozzle 115.

If the fluid is to be transferred to the patient as by gravity then the air inlet valve is opened by pulling the finger gripping ring 74 outwardly to permit air to enter into the container 150. If additional force is required for administration then the air valve is closed by moving the finger gripping ring 74 to cause the valve to close. The accordion container may then be pushed to cause the ends to be moved toward each other with or without manipulating hand grips 152 and 154. If withdrawal of a portion of the enema solution from the patient is desired then the ends of the container are moved away from each other by manipulating the finger grips 152 and 154 and pulling them outwardly. Prior to this expanding of the container the air inlet valve controlled by the finger gripping ring 74 is pushed to a closed condition. By manipulating this air inlet valve and also the accordion container 150 the desired inflow and withdrawal of the mixed fluid may be manipulated as desired by the attendant.

ALTERNATE CONFIGURATION OF FIG. 19

Depicted in FIG. 19 is a bellows-type syringe similar to that of FIG. 13, however, in this particular embodiment a bellows-type syringe body 50b has an outlet in which an adapter 278, similar to the adapter 78 in FIG. 13, is mounted. This adapter is secured to a flexible conduit 280 which as formed is initially substantially round. This conduit has ribs 281 disposed at the outer portion thereof to insure a stiffness in a localized portion of this wall so that when the conduit is bent the side opposite the ribs achieves a pinching action and a shut off is provided at the indicated bend. Gripping fingers 82 carried by the body are similar or identical to the gripping fingers 82 shown in FIG. 13. Guide and support fingers 283 are provided at the right bottom of the body 50b in order to retain the outer portion of nozzle 15a during packaging, shipping and prior to use.

ALTERNATE FOLDING VALVE OF FIG. 20

Referring next and finally to FIG. 20 there is shown a folding valve similar to that shown in FIG. 19 but instead of the conduit incorporated as a portion of the syringe nozzle, this folding valve is adapted to receive the upper or receiving end of a length of tubing which may be used with an enema nozzle or other syringe device. As depicted in FIG. 20, the conduit portion 380 has a pair of stiffening ribs 381 disposed at 70° to 90° from each other. These ribs insure that as the circular tubing portion 380 is bent to a more or less right angle that a sharp bend opposite the ribs is formed and causes a positive cutoff of flow and provides an inexpensive plastic cutoff valve. The upper portion 384 is made to be a tight press fit in an outlet aperture in the bellows bottle. This conical end has a sharp inner edge which will cut through a thin plastic seal as seen in FIGS. 14 and 18 or if the entryway into the bottle is open into the bellow-type bag and no membrane is present this end is tight fitting in this outlet. Ferrule portions 385 are provided at the discharge end of the conduit and engage the inside of a resilient tube of rubber or plastic to tightly retain a length of tubing whose other end is connected to a nozzle. It is to be noted that the ribs 381 or 281 which are formed on the fold-over valves of FIGS. 19 and 20 not only assist in positioning of the foldover valve at the time of assembly but also insure that the bending of the conduit takes a desired configuration during which a short portion is bent sufficiently to provide a positively closed valve for the purpose of retaining either powder, fluid or a mixture thereof in the bellows bag.

It is, of course, to be realized that either the keyhole clamp shutoff 40, the folding valve as shown in FIGS. 13, 19 and 20 or the sliding valve of FIG. 10 may be utilized in any syringe arrangement to provide a desired result. It is also to be noted that the handle portions 152 and 154 shown in FIG. 18 alternately may be molded so as to extend inwardly of the end surfaces instead of outwardly from the end portions of the accordion container. On the container 50 of FIG. 9 fluid or air control inlet means may be provided on the top of this accordion-type container, if desired.

Terms such as "up", "down", "bottom", "top", "front", "back", "in" "out" and the like are applicable to the embodiments shown and described in conjunction with the drawings. These terms are merely for the purposes of description and do not necessarily apply to the position in which the syringes and the flow control valve means may be constructed or used.

While particular embodiments of the bag and valve construction have been shown and described it is to be understood that modifications may be made within the scope of the accompanying claims and protection is sought to the broadest extent the prior art allows.

What is claimed is:

1. A syringe for vaginal douche and enemas and the like, said syringe including: (a) a flexible container having an accordion configuration; (b) a discharge conduit adapted for fluid-tight connection to the container; (c) a manipulative shutoff valve associated with said discharge conduit, said valve when open permitting the flow of fluid from the container, said conduit being semiflexible and having a substantially circular cross section, the conduit having at least one stiffening rib locally formed as a part of the outer surface of the conduit and providing an assist to insure bending of the conduit into a pinch configuration to provide fluid-flow cutoff when the conduit is bent substantially at a right angle to and away from the stiffening rib whereby in this bent condition the sides of the conduit are brought together to inhibit flow therethrough; (d) means for releasably retaining this conduit in the bent condition during storage and shipment until the conduit is straightened for fluid flow and use, and (e) a discharge nozzle attachably associated with the outlet end of the conduit.

2. A syringe as in claim 1 in which the portion of the conduit which is to be bent includes two stiffening ribs extending axially along the conduit, said ribs being about 70 to 90° apart.

3. A syringe as in claim 1 in which that terminal end of the conduit portion of the shutoff valve which is below the pinch fold includes ferrule-like means formed on the conduit, said means adapted to receive and retain the inlet end of a length of tubing leading to the discharge nozzle.

4. A syringe for vaginal douche and enemas and the like, said syringe including: (a) a flexible container of accordion configuration; (b) a discharge tube having a connected semi-flexible conduit having a substantially circular cross section, said conduit having at least one stiffening rib locally formed as a part of the outer surface of the conduit connected to the container in a fluid-tight manner; (c) at least one of the component portions of a fluid mix to be used with said syringe contained in this flexible container; (d) a manipulative cutoff valve associated with said discharge tube, said valve when open permitting the flow of fluid from the container, this valve being brought to a closed condition with a bending of the conduit into a pinch configuration resulting in the fluid-flow cut off when the conduit is bent substantially at a right angle to and away from the stiffening rib whereby in this bent condition the sides of the conduit are brought together to inhibit fluid flow therethrough; (e) means for releasably retaining this conduit in the bent condition during storage and shipment until the conduit is unbent for fluid flow and use, and (f) a discharge nozzle attachable to the outlet end of the discharge tube.

5. A syringe as in claim 4 in which the means for releasably retaining the bent conduit is a pair of opposed gripping fingers carried by the and on the accordion container.

6. A syringe as in claim 4 in which the portion of the conduit which is to be bent includes two stiffening ribs extending axially a short distance along the conduit, said ribs being about 70° to 90° apart.

7. A syringe as in claim 4 in which that terminal end of the conduit portion of the shutoff valve which is below the pinch fold includes a ferrule-like means formed on the conduit, said means adapted to receive and retain the inlet end of a length of tubing disposed to be connected to a discharge nozzle.

* * * * *